(12) United States Patent
Shaffer et al.

(10) Patent No.: US 8,408,202 B2
(45) Date of Patent: Apr. 2, 2013

(54) OPEN-CIRCUIT LIQUID VENTILATOR

(75) Inventors: Thomas H. Shaffer, Chadds Ford, PA (US); Marla R. Wolfson, Wyndmoor, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 780 days.

(21) Appl. No.: 12/449,331

(22) PCT Filed: Jan. 25, 2008

(86) PCT No.: PCT/US2008/000974
§ 371 (c)(1), (2), (4) Date: Aug. 3, 2009

(87) PCT Pub. No.: WO2008/097433
PCT Pub. Date: Aug. 14, 2008

(65) Prior Publication Data
US 2010/0012122 A1 Jan. 21, 2010

Related U.S. Application Data

(60) Provisional application No. 60/899,489, filed on Feb. 5, 2007.

(51) Int. Cl.
*A61M 16/00* (2006.01)
*A61M 15/00* (2006.01)
(52) U.S. Cl. .............................. 128/203.25; 128/203.15
(58) Field of Classification Search ............. 128/200.14, 128/200.21, 201.13, 202.26, 203.12, 203.16, 128/203.17, 203.26, 204.14, 204.17, 913; 604/23–26; 424/673
See application file for complete search history.

(56) References Cited

U.S. PATENT DOCUMENTS

| | | | |
|---|---|---|---|
| 5,158,536 A | 10/1992 | Sekins et al. | 604/20 |
| 5,335,650 A | 8/1994 | Shaffer et al. | 128/200.24 |
| 5,350,359 A | 9/1994 | Shaffer et al. | 604/51 |
| 5,429,123 A | 7/1995 | Shaffer et al. | 128/204.23 |
| 5,540,225 A | 7/1996 | Schutt | |
| 5,562,608 A | 10/1996 | Sekins et al. | 604/20 |
| 5,590,651 A | 1/1997 | Shaffer et al. | 128/632 |
| 5,707,352 A | 1/1998 | Sekins et al. | 604/56 |
| 5,741,248 A | 4/1998 | Stern et al. | 606/21 |
| 5,788,665 A | 8/1998 | Sekins | 604/19 |
| 6,105,572 A | 8/2000 | Shaffer et al. | 128/200.24 |
| 6,166,092 A | 12/2000 | Sekins et al. | 514/772 |
| 6,242,472 B1 | 6/2001 | Sekins et al. | 514/396 |
| 2004/0236241 A1 | 11/2004 | Murphy | |
| 2006/0278224 A1 | 12/2006 | Shaffer et al. | |

OTHER PUBLICATIONS

Greenspan, et al., "Liquid Ventilation of Preterm Baby", *The Lancet*, 2 (8671): 1095 (1989).

*Primary Examiner* — Stephen Crow
(74) *Attorney, Agent, or Firm* — Drinker Biddle & Reath LLP

(57) ABSTRACT

An open-circuit liquid ventilation system includes a reservoir containing a breathable liquid, a patient interface receiving breathable liquid from the reservoir, a pump directing breathable liquid from the reservoir to the patient, a controller for the pump, and a tank for storing used breathable liquid. The system may be passive regarding expired liquid. Alternatively, the system may be active and include a bypass line connected to the pump such that used breathable liquid is drawn from the patient. The patient interface may be adapted to interface a gas ventilation system to facilitate a rapid conversion from gas to liquid ventilation. The system may include sensors monitoring pressure and volume parameters and may include an output displaying information including schematics and real time tracings regarding a ventilation procedure.

16 Claims, 3 Drawing Sheets

OPEN-CIRCUIT LIQUID VENTILATOR

CROSS-REFERENCE TO RELATED APPLICATION

This application claims priority from U.S. provisional application No. 60/899,489, filed Feb. 5, 2007, the entire disclosure of which is hereby incorporated by reference.

FIELD OF THE INVENTION

The present invention relates generally to liquid ventilation using breathable liquids for pulmonary recruitment and conditioning to treat pulmonary disorders or disease and, more particularly to an open-circuit liquid ventilation system and method of use.

BACKGROUND OF THE INVENTION

In the human circulatory system, blood first goes to the lungs for oxygenation before being directed to the rest of the body. When the lungs do not function properly, such as for a patient with Respiratory Distress Syndrome (RDS), collapsing of the lungs often requires the use of a ventilator to provide proper respiration. It is known to utilize liquid ventilation systems for pulmonary recruitment and conditioning to treat pulmonary disorders or disease such as RDS. Procedures using liquid ventilation are sometimes referred to as "liquid assisted ventilation" (LAV) procedures. In a LAV procedure, a breathable liquid is instilled into the patient's pulmonary system (e.g., lungs), typically via the patient's trachea, to replace the nitrogen gas that otherwise is the means for carrying oxygen and carbon dioxide during respiration.

Despite significant advances in respiratory care and reduction in mortality of patients with respiratory failure, morbidity persists and often results from iatrogenic mechanisms. In particular, preterm infants weighing less than approximately 1500 gm experience significant acute and chronic respiratory complications. More importantly, during an era of increasing multiple births secondary to infertility management, a greater number of very low birth weight and very preterm infants are born. Those infants weighing less than approximately 500 gm who survive the initial respiratory syndrome of prematurity, commonly (i.e., approximately 85%) experience significant chronic lung disease with neurodevelopmental delay. In this regard, these fragile infants represent an underserved population with respect to existing respiratory therapies.

LAV procedures present a promising modality in the treatment of respiratory distress for both an immature lung or an injured mature lung. It has been found that LAV may confer a cytoprotective benefit to the lung, either by a serving as a mechanical barrier or by direct cytoprotective action. LAV has been associated with a reduction in the number of, as well as the amount of, mediators released by pulmonary inflammatory cells. Mechanisms for cytoprotection may be related to the mechanical reduction of intercellular surface tension, perfluorochemical ("PFC") miscibility in lipid membranes, cellular PFC ingestion, as well as PFC effect on intercellular adhesions molecules. As such, LAV appears to provide both mechanical and anti-inflammatory protection.

The terms "breathable fluid" and "breathable liquid" both refer to a liquid (i.e., a non-gas) having the ability to deliver oxygen into, and to remove carbon dioxide from, the pulmonary system of a patient. Examples of breathable liquids include, but are not limited to, saline, silicone and vegetable oils, perfluorochemicals ("PFC"), and the like. Presently, PFC liquids are preferred, particularly perfluorocarbon liquids. PFC liquids are clear, colorless, odorless, nonflammable, and essentially insoluble in water. PFC liquids have an extremely high affinity for gases making them very desirable as the means for delivering oxygen to a patient and returning carbon dioxide from the patient. They have low surface tension and, for the most part, low viscosity. They also have anti-oxidative properties and exhibit anti-inflammatory characteristics.

Beneficial uses for PFC liquids in a LAV procedure are numerous. They include: (1) improved gas exchange; (2) opening of atelectatic areas by recruitment to increase total lung capacity; (3) acting as a surfactant to open a collapsed alveoli; (4) acting as a vehicle to deliver biological or non-biological agents; (5) homogenously expanding lung to decrease the risk of overexpansion or underexpansion; (6) removal of debris; (7) decreasing risk of oxygen toxicity; (8) decreasing inflammation in the lung; and (9) increasing pulmonary blood flow to an injured lung area creating better oxygenation. In addition, pulmonary debris (i.e. exudate, meconium, mucous) is readily moved by tidal PFC volumes.

Due to low surface tension, high respiratory gas solubility, and high spreading coefficients of the PFC liquid, the placement of the PFC liquid into the patient's pulmonary system replaces the normally gas-liquid interface with a liquid-liquid interface having low interfacial tension at the lung surface. The PFC liquid also supports an adequate alveolar reservoir for the pulmonary gas exchange. As a result of the reduced interfacial tensions at the lung surface, transmural pressures across the alveolar-capillary membrane are more evenly matched in the liquid-filled lung compared to a gas-filled lung. This promotes more homogeneous pulmonary blood flow in the liquid-filled lung. The addition of a surfactant to the PFC liquid may further reduce collapsing pressures in the PFC-treated lung by further decreasing tension at the PFC-lung interface.

It is also known to use PFC liquid during a LAV procedure as a means of delivering a drug or biologic agent into the lung parenchyma instead of delivering the drug intravenously. Most drugs administered intravenously for a respiratory target enter the lung tissue by passive diffusion. However, such passive diffusion of the drug depends upon the free plasma drug concentration in the pulmonary capillaries, which is often inadequate in the case of a patient with an impaired lung. Lung tissue uptake of an intravenously administered drug also depends upon the ratio of the surface area of the diffusion membranes (i.e., the capillaries) to the extravascular fluid volume in the lung. This ratio, however, is typically low for a patient with an injured lung, thus impairing the uptake of the drug for such a patient.

The above-described properties of PFC liquids also make PFC liquids desirable for intratracheal administration of a drug. Respiratory gas solubility of the PFC liquid supports gas exchange, while the low surface tension and ability to recruit lung volume also allows for drug distribution to the under-ventilated lung regions. Additionally, the inert nature of the PFC liquid precludes any drug-vehicle interactions. When drugs are suspended in the PFC liquid and delivered during tidal liquid ventilation (TLV), it is possible to control the delivery rate, the time of injection, and the total amount of drug delivered to the lung. Thus, intratracheal drug administration during LAV desirably targets the lung compared to an intravenous administration.

Known LAV techniques include total liquid ventilation (TLV), partial liquid ventilation (PLV), PFC-lavage, and aerosol-PFC. In a TLV technique, transport of the respiratory gases is achieved solely in dissolved form through the tidal volume exchange of the PFC liquid to and from the lung. As such, a total liquid ventilation procedure is sometimes also referred to as "tidal liquid ventilation." As discussed above, all of the gas-liquid interfacial tension is desirably eliminated in TLV. Lung volume is recruited and compliance is increased in TLV while inflation pressures and pulmonary barotrauma are reduced.

In a PLV technique, the lung is instilled and maintained with a functional residual capacity (FRC) of the PFC liquid while mechanical gas ventilation is being performed. In this way, a PLV technique utilizes the alveolar recruitment capabilities of the low surface tension PFC liquid to establish an adequate FRC in an impaired lung. The simultaneous mechanical gas ventilation provides for the exchange of $CO_2$ and oxygen in the lung. Effective ventilation of a lung using PLV is more challenging than TLV because of the increased number of unknown factors in the lung only partially filled with liquid. These unknown factors relate to the distribution of the PFC liquid in the lung, the saturation of oxygen and carbon dioxide in the resident PFC, the continually changing lung mechanics, the evaporative loss of PFC, and the changing volumes of gas and PFC volumes in the lung.

Maintenance of a therapeutic PFC liquid volume following initial instillation in the lungs is dependent upon a number of factors. PFC liquids with different physicochemical properties such as kinematic viscosity, spreading coefficients and $CO_2$ solubility demonstrate diverse patterns of distribution and elimination. For example, a liquid with higher kinematic viscosity tends to distribute less homogeneously but also resists redistribution over time, and thus maintains greater contact with the inspired gas and eliminates relatively faster than a liquid of lower kinematic viscosity and comparable vapor pressure. Liquids of higher vapor pressure will volatize into the expired gas more rapidly than lower vapor pressure liquids. PFC liquid volume loss and evaporation rate from the lungs is influenced by many factors including time, PFC vapor pressure, gas to liquid contact, ventilation strategy, lung pathophysiology, repositioning of the subject, and the administration of supplemental PFC doses to the lungs. It has been found that additional instrumentation is necessary during PLV in order to determine evaporative loss, to guide and sustain dosing levels, and to reduce dose consumption. Also, pulmonary debris will tend to migrate from the distal to proximal lung during PLV. Frequent suctioning to remove debris, therefore, is needed during a PLV procedure.

In a lavage procedure, a liquid (i.e., a PFC liquid) is used to wash out an organ. Thus, in a LAV procedure utilizing PFC-lavage, a PFC liquid is used to wash out the lung. PFC-lavage techniques can also be used for other purposes such as heat transfer to heat or cool a patient. In an aerosol-PFC procedure, the PFC liquid is in an aerosolized form. The aerosolized PFC is typically instilled into the patient via an introducible jet-nebulizer.

Examples of liquid ventilation systems are disclosed in U.S. Pat. No. 5,158,536 (see FIGS. 29 and 34) and U.S. Pat. No. 6,105,572 (see FIGS. 1 and 2). As shown, the liquid ventilation systems are closed-circuit systems because the PFC liquid is circulated in cyclic fashion between the patient and a storage reservoir or regenerator. As described in the '572 patent, expired PFC liquid from the patient is conditioned (i.e., regenerated) in the closed-circuit before being returned to the patient in a subsequent cycle primarily by removing carbon dioxide from, and adding oxygen to, the PFC liquid. The PFC liquid may also be conditioned to adjust temperature or to condense fluorocarbon vapors generated during a therapeutic procedure as a means of conservation.

SUMMARY OF THE INVENTION

According to the present invention, an open-circuit liquid ventilation system is provided. The open-circuit system of the present invention is adapted for rapid recruiting and conditioning of a patient's pulmonary system for a short duration. The open-circuit system includes a supply reservoir containing a supply of a breathable liquid, most preferably a PFC liquid in a sealed container. The PFC liquid is preferably preconditioned by oxygenating (potentially hyperoxygenating) the PFC liquid and removing carbon dioxide. The PFC liquid can also be thermally conditioned. According to one preferred method, a sealed supply reservoir is selected containing a quantity of preconditioned PFC liquid appropriate for recruiting and conditioning a particular patient (e.g., a patient having a weight within a certain range) for a relatively short period of time (e.g., ten minutes).

The PFC liquid of the open-circuit liquid ventilation system, in contrast to that of closed-circuit systems, is used once and is not recycled by the system for return to the patient. The open-circuit system of the present invention includes an expired PFC tank for receiving the PFC liquid from the patient.

The open-circuit liquid ventilation system includes an interface valve system adapted to act as an interface between the patient, the PFC liquid, and a conventional respiratory support system such as a gas ventilator. This arrangement enables rapid transition between respiratory support utilizing the gas ventilator and liquid ventilation utilizing the open-circuit liquid ventilation system.

The open-circuit liquid ventilation system includes a pump between the reservoir and the interface valve system for directing PFC liquid from the reservoir to the patient. The open-circuit liquid ventilation system also includes a CPU, preferably associated with the pump, adapted to provide microprocessor control over the operation of the liquid ventilation system according to an algorithm of the CPU.

The system preferably includes sensors for monitoring various parameters associated with the liquid ventilation of a patient, particularly pressure and volume parameters, for use by the CPU to control the operation of the open-circuit liquid ventilation system.

According to one embodiment, PFC liquid is removed from the pulmonary system (e.g., lungs) of the patient passively (e.g., automatically) in response to recoil pressure of the patient's lungs and hydrostatic pressure of the PFC liquid. According to another embodiment, PFC liquid is removed from the patient actively using the pump of the open-circuit system. A bypass line and valve are included between the PFC reservoir and the pump. During inspiration, the bypass line is closed allowing the PFC liquid to be directed by the pump to the patient via the interface valve system similar to delivery in the passive expiration system. When predetermined pressure or volume parameters are monitored by the sensors, the system switches the bypass valve to open the bypass line such that the pump can be used to draw liquid from the patient for discharge to the expired PFC tank.

According to one embodiment, the system provides a display of information regarding the operation of the open-circuit liquid ventilation system, in particular the dynamic pressure-volume relationships during transient filling and emptying of the lungs with the PFC liquid. The display preferably includes calibrated/scaled tracings representing real-time values of pressure and volume parameters measured by the sensors. According to a presently preferred embodiment, the display includes graduated vertical bars located on opposite sides of the tracings that are coded (e.g., using color) to indicate values within certain defined ranges such as values within desired or expected operating ranges, values within marginal zones adjacent the operating ranges and values outside of the marginal ranges. The open-circuit liquid ventilation system may also be adapted to activate visual and/or auditory alarms, and to trigger system valves to divert the flow of PFC liquid accordingly, in the event that values outside of the marginal zones (i.e., danger values) are monitored.

As used herein, the term "breathable liquid" refers to liquids which have the ability to deliver oxygen into, and to remove carbon dioxide from, the pulmonary system of a patient.

As used herein, the terms "open-circuit liquid ventilation system" and "open-circuit manner" refer to a liquid ventilation system in which a breathable liquid is delivered once to a patient and is not recycled by the system as in a closed-circuit liquid ventilation system.

As used herein, the term "pre-conditioned" as applied to a breathable liquid contained in a supply reservoir refers to a breathable liquid that has been treated, for example by oxygenating the liquid, prior to placement of the breathable liquid into the reservoir. As used herein, the term "reconditioning" as applied to a breathable liquid refers to treatment of a breathable liquid (e.g., to remove carbon dioxide from the liquid) after the liquid has been delivered to the pulmonary system of a patient and subsequently discharged from the pulmonary system of the patient.

As used herein, terms such as "recruit", "recruiting", "recruitment" as applied to the pulmonary system of a patient mean the replenishment or restoration of an impaired component of the pulmonary system (e.g., a collapsed lung).

As used herein, terms such as "condition" and "conditioning" as applied to the pulmonary system of a patient mean the placement of a component of the pulmonary system (e.g., a lung) into a state of proper operation.

As used herein, the terms "expired" and "used" as applied to a breathable liquid refer to a breathable liquid that has been delivered to the pulmonary system of a patient and subsequently discharged from the pulmonary system of the patient.

BRIEF DESCRIPTION OF THE DRAWINGS

For the purpose of illustrating the invention, the photographs and drawings show a form of the invention that is presently preferred. However, it should be understood that this invention is not limited to the precise arrangements and instrumentalities shown.

DESCRIPTION OF THE INVENTION

Figure 1:
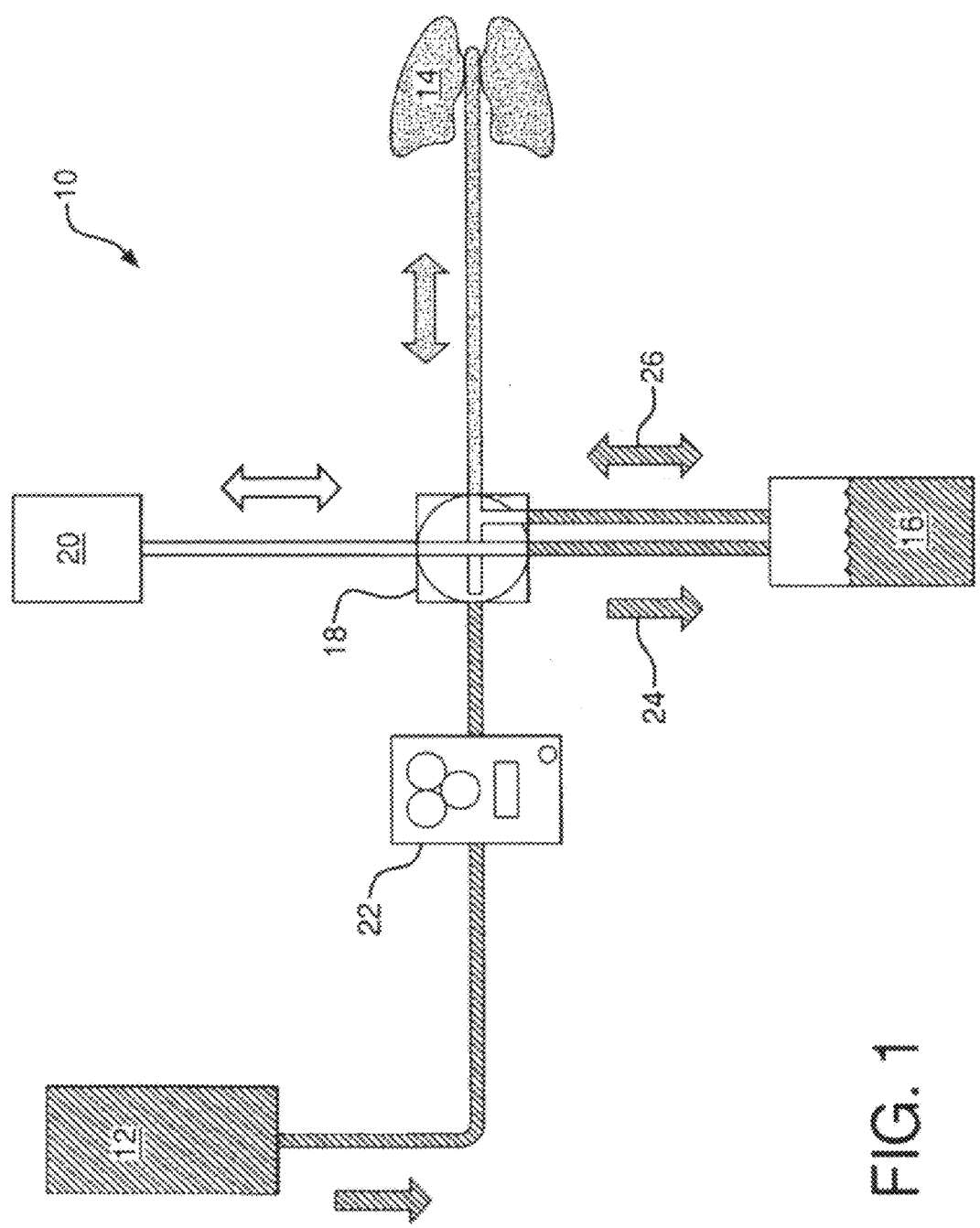
FIG. 1 is a schematic illustration of an open-circuit liquid ventilation system according to a first exemplary embodiment of the invention utilizing passive expiration.

Referring to the drawings where like numerals identify like elements, there is shown in FIG. 1 an open-circuit liquid ventilation (LV) system 10 according to a first exemplary embodiment of the invention. As described below in greater detail, the present invention provides a compact and simplified open-circuit system that provides for a rapid transition between a gas-filled lung to a liquid filled lung for short term recruitment and conditioning of an impaired lung. According to one presently preferred embodiment, the open-circuit system is adapted for a single use with a particular patient (e.g., a patient of a certain weight) followed by disposal of the system.

The open-circuit LV system 10 includes a breathable liquid supply reservoir 12 containing a supply of a breathable liquid. As used herein, the term "breathable liquid" refers to liquids which have the ability to deliver oxygen into, and to remove carbon dioxide from, the pulmonary system of a patient, in particular the lungs. Although the invention is not limited to any particular breathable liquid, perfluorochemical ("PFC") liquids are presently preferred, particularly perfluorocarbon liquids. PFC liquids are chemically inert, clear, colorless, odorless, non-conducting, nonflammable, substantially insoluble in water, non-toxic and biocompatible. PFC liquids are extremely stable compounds that are not metabolized in body tissues. They have low surface tension and, for the most part, low viscosity. PFC liquids also have extremely high affinity for gases capable of dissolving up to twenty (20) times as much oxygen and over three (3) times as much carbon dioxide as water.

As described below in greater detail, the PFC liquid of the LV system 10 is directed from the breathable liquid (PFC) supply reservoir 12 to the pulmonary system of a patient 14. The PFC liquid, however, is not returned (i.e., recycled) to the PFC supply reservoir 12 from the patient 14 as in prior LV systems and, instead, is directed in an open-circuit manner to an expired PFC tank 16. Preferably, the PFC supply reservoir 12 is prepackaged and disposable. As part of the packaging of the LV system 10, the PFC liquid is preferably sealed within the PFC supply reservoir 12 in a sterile condition. Preferably, the PFC supply reservoir is sized to contain a quantity of PFC liquid appropriate for a particular application to optimize cost of consumables by matching supply capacity to an anticipated need based on patient weight. For example, a 1 kg infant breathing 4 breaths per minute at a tidal volume of 15 ml/kg for 10 minutes would require a PFC supply reservoir 12 containing approximately 600 milliliters for the 10 minutes. The PFC liquid contained in the supply reservoir 12 could be pre-conditioned as part of the prepackaging of the LV system 10 to oxygenate the PFC liquid. The PFC could also be pre-treated to suspend an additive such as a drug for delivery to the patient's pulmonary system using the open-circuit LV system 10. Preferably, the PFC liquid contained in the PFC supply reservoir 12 is also heated prior to delivery to the patient 14.

The open-circuit LV system 10 includes an interface valve system 18 adapted to provide an interface between the LV system 10, the patient 14 and a conventional respiratory support system, such as gas ventilator 20. The interface valve system 18 desirably allows the clinician to simply interface the patient's endotracheal tube with the LV system 10 and the conventional gas ventilator 20 to enable rapid transition between delivery of a gas medium to the patient 14 from the gas ventilator 20 to delivery of the PFC liquid to the patient using the LV system 10. As described below, the interface valve system 18 also is adapted to provide mechanical relief in order to limit inspiratory and expiratory pressures.

The open-circuit liquid ventilation system 10 is regulated by interactive control processes, in a similar way that known closed-loop TLV systems have process control algorithms, that are implemented by a servo-control unit. The open-circuit LV system 10 includes a pump 22 having a central processing unit ("CPU") adapted to provide microprocessor control over the liquid ventilation of the patient 14 using the LV system 10. Preferably, the system includes a manual override feature. The system 10 preferably includes electronic sensors adapted to monitor pressure and volume in the system. The sensors could be included with the pump 22 in an in-line fashion. Alternatively, the sensors could be located at a different location. An algorithm of the pump CPU could include routines for, but is not limited to, delivering a certain volume of PFC liquid in a certain time period under specified pressure limitations in order to safely and effectively recruit an atelectatic lung while limiting the risk of volume or pressure trauma to the patient's lung.

With the patient 14 on respiratory support and receiving gas from the gas ventilator 20 via the interface valve system 18, liquid ventilation of the patient 14 is initiated by switching the interface valve system 18 from the gas ventilator 20 to the open-circuit LV system 10. As described above, the supply reservoir 12 of the LV system 10 is preferably pre-filled with an amount of sterile, warmed, and oxygenated PFC liquid that is preferably appropriate for the size of the patient 14. During inspiration, the fresh PFC liquid is pumped by the pump 22 under control by the CPU from the supply reservoir 12 through the interface valve system 18 to the patient 14. It is desirable to recruit the lung (or lungs) of the patient 14 to a specific PFC volume (e.g., 10-15 mL/kg) in order to maintain sufficient area to provide for proper gas exchange, optimal lung mechanics and hemodynamics. Recruitment is achieved by instilling the volumes of PFC liquid into the lung(s) of the patient 14 directly through the endotracheal tube.

When the specified volume of PFC liquid for proper lung treatment has been measured by the electronic sensors of the system, the CPU of the pump 22 directs the LV system 10 to close the port of the interface valve system 18 to the PFC supply reservoir and to open a normally closed port of the interface valve system 18 to the expired PFC tank 16. In this manner, PFC liquid which is discharged from the patient 14 during expiration is directed through the interface valve system 18 to the expired PFC tank 16 as indicated by arrow 24. The LV system 10 is preferably also adapted with a safety feature to close the port to the supply reservoir and open the port to the expired PFC tank in the event that a certain pressure is measured by the electronic sensors of the system. The above safety feature is preferably backed up mechanically by including a spring-loaded pressure-relief valve in the interface valve system 18 that is adapted to automatically open in response to a certain pressure to direct PFC liquid to the expired PFC tank 16 (as indicated by arrow 26), thereby preventing excess pressure in the LV circuit from harming the patient 14.

The expiration of PFC liquid from the patient 14 to the expired PFC tank 16 in the LV system 10 of FIG. 1 is passive. Thus, the PFC liquid is directed from the patient 14 to the expired PFC tank 16 via the interface valve system 18 automatically in response to recoil pressure of the patient's lung and hydrostatic pressure of the PFC liquid. Preferably, the expired PFC tank 16 is graduated with volumetric demarcations to provide visual feedback to the operator regarding volume inventory of the PFC liquid.

Figure 2:
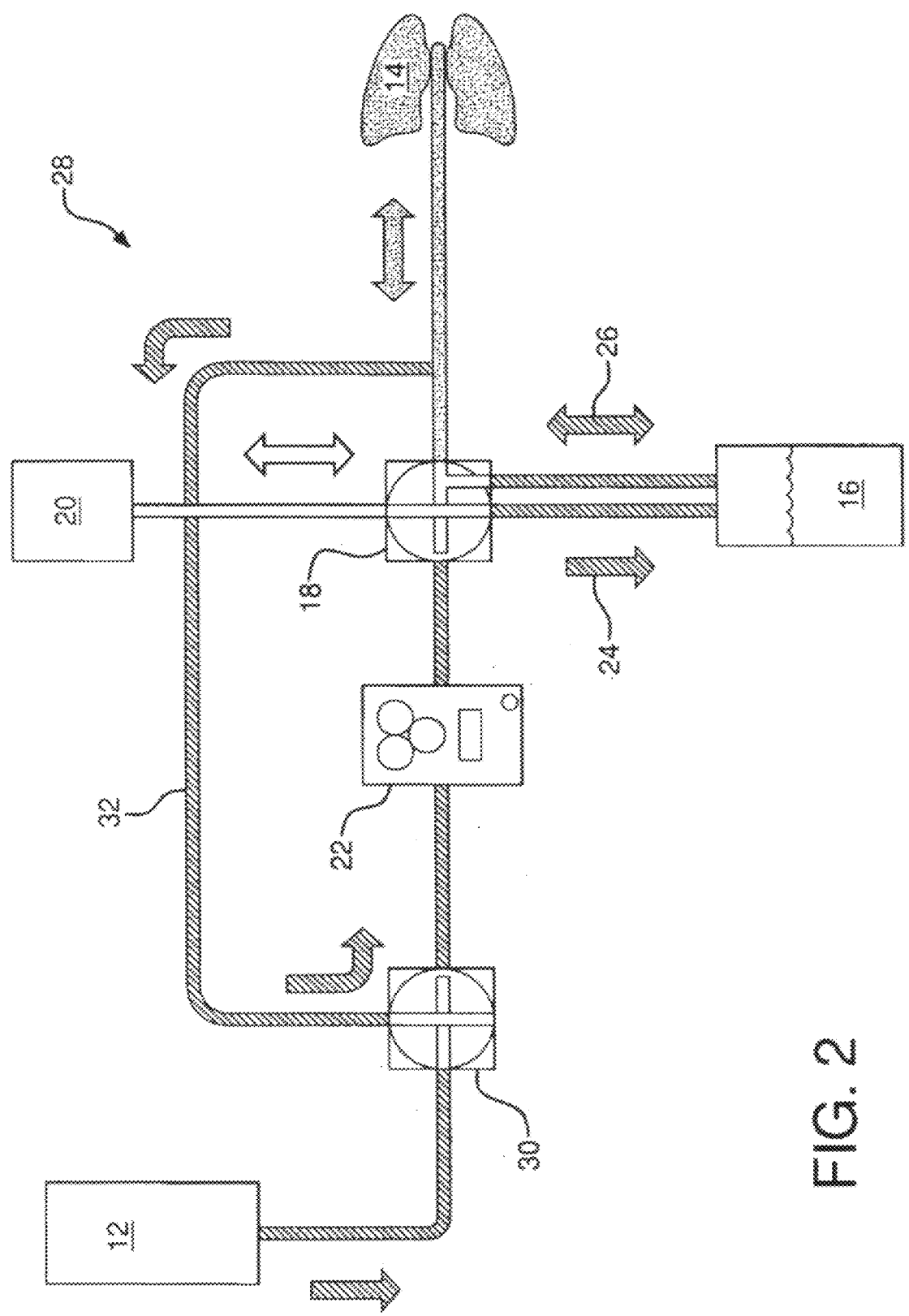
FIG. 2 is a schematic illustration of an open-circuit liquid ventilation system according to a second exemplary embodiment of the invention utilizing active expiration.

Referring to FIG. 2, there is illustrated a LV system 28 according to a second exemplary embodiment of the invention adapted for active removal of PFC liquid from the patient 14 to the expired PFC tank 16. As shown, the LV system 28 includes a valve 30 located in the line between the PFC reservoir 12 and the pump 22 and a bypass line 32 connecting the valve 30 to the line that links the patient 14 to the interface valve system 18.

Inspiration of fresh PFC liquid from the pre-filled supply reservoir 12 to the patient 14 is accomplished in the LV system 28 in a similar manner as described above for the LV system 10. Thus, the interface valve system 18 is switched to close the port to the gas ventilator 20 and open the port of the interface valve system 18 to the LV circuit. During inspiration, the valve 30 of the active PFC removal system between the pump 22 and the PFC supply reservoir 12 is open to the supply reservoir 12 and closed to the bypass line 32. This allows fresh PFC liquid to pass through the valve 30 to the pump 22 and the interface valve system 18, under control of the CPU of the pump 22, to be directed to the patient 14 in a similar manner as described above for LV system 10.

When predetermined pressure or volume during inspiration of PFC liquid is measured by electronic sensors, the LV system 28 is switched as follows to provide active removal of PFC liquid by pump 22 during expiration. The valve 30 between the supply reservoir 12 and the pump 22 is closed to the reservoir 12 and opened to the bypass line 32. The interface valve system 18 is closed to the patient 14 and opened to the expired PFC tank 16. As such, the pump 22 in the removal mode is adapted to draw used PFC liquid from the patient 14 via bypass line 32 and valve 30. The used PFC liquid is then directed from the pump 22 to the expired PFC tank 16 via the interface valve system 18 through the port that is opened to the tank 16.

As discussed above, the operation of the LV systems 10, 28 are controlled by the CPU of the pump 22 in response to electronic sensors of systems 10, 28 monitoring volume and pressure. The pressure and volume values that are monitored preferably include tidal volumes, delivery pressure, and total PFC lung volume delivered. The servo-control of the PFC liquid delivery could also be responsive to other measured parameters such as respiratory timing.

Figure 3:
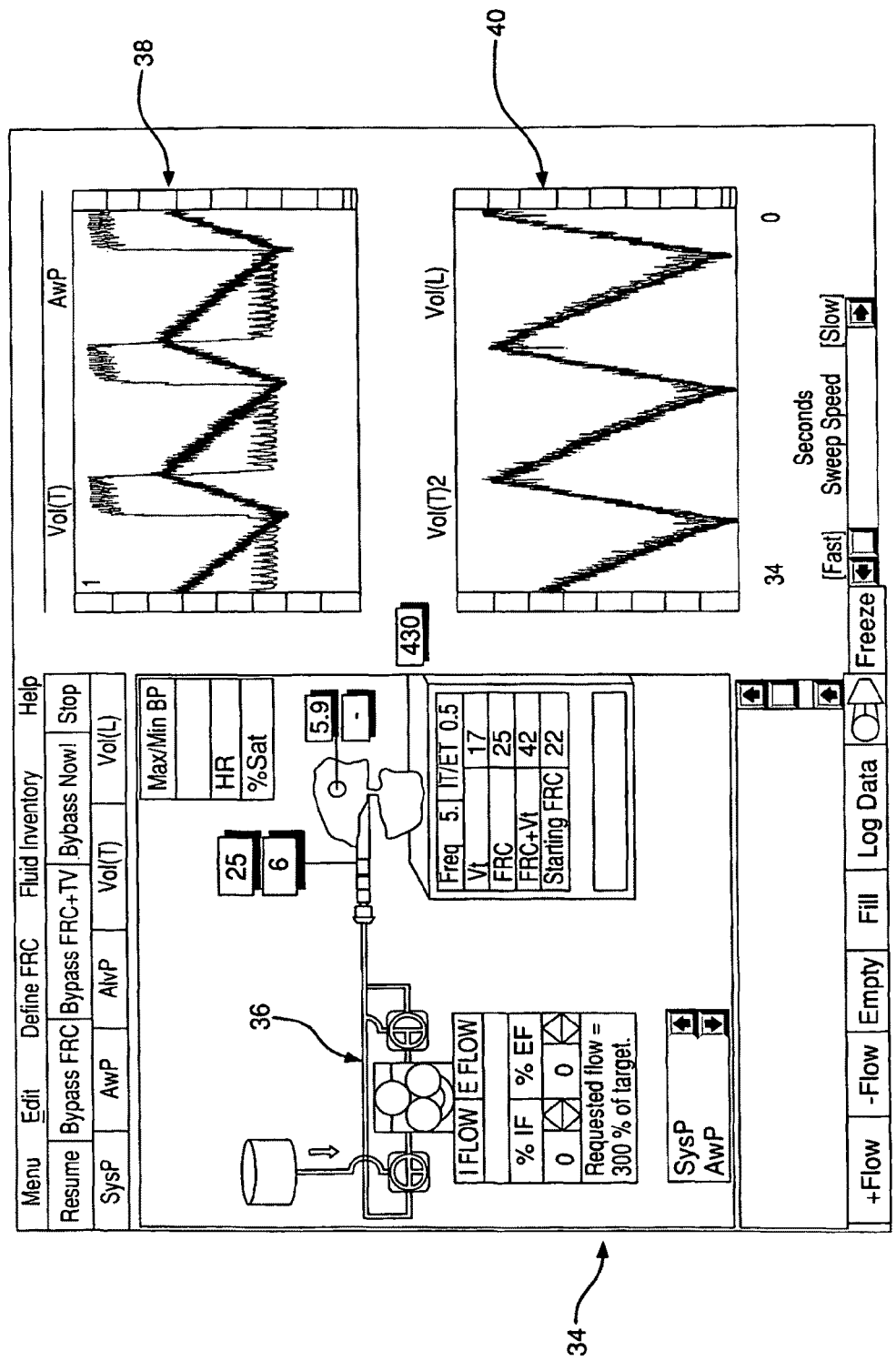
FIG. 3 illustrates an output display including graphical information from a CPU of an open-circuit liquid ventilation system according to the invention.

Referring to FIG. 3, there is illustrated a computer-generated display 34 presenting output information regarding the operation of an LV system, such as systems 10, 28, and providing for user inputs to control various features of the LV system. The display provides information regarding dynamic pressure-volume relationships during transient filling and emptying of the lung with the PFC liquid as controlled by the CPU of the pump 22.

On the left hand side of the display 34, a schematic illustration 36 of the LV system being monitored is shown with numerical values identifying certain system parameters. On the right hand side of the display 34, graphical displays including calibrated/scaled tracings 38, 40 representing real-time values of pressure and volume measurements from the electronic sensors of the LV system 10, 28 are shown. The graphical displays include graduated vertical bars located on opposite sides of the tracings. The graduated bars preferably are coded (e.g., using color) to indicate values within certain defined ranges. For example, values within desired operating ranges could be shown in green, those within 10 percent of the operating zone could be shown in yellow, and those outside of predetermined operating and marginal limits could be shown in red. When either pressure and volume measurements are outside of the operating or marginal ranges (i.e., when measurements are in the red zones), the system could be adapted to activate visual and auditory alarms and to trigger system valves to divert the flow of PFC liquid accordingly.

Additional visual display could include a pressure-volume loop display in which optimal morphology consists of loops lacking flattening at either end-inspiration or expiration, thus preventing over-inflation or under-inflation. U.S. Pat. No. 5,429,123 shows pressure-volume loops of this type (see FIGS. 2-7). The operation of the system 10, 28 could also be guided by clinical feedback such as pulse oximetry (e.g., SpO2≧90%), end-tidal $CO_2$ (e.g., 40-60 mmHg), and expected vital signs for a certain age.

The variables used in display 34 to represent system parameters are as follows: IFLOW=inspiratory flow; EFLOW=expiratory flow; TV=tidal volume; SysP=system pressure; AwP=airway pressure; AlvP=alveolar pressure; Vol (T)=tidal volume tracing; Vol(T)=duplicate tidal volume tracing; Vol (L)=lung volume; Vt=tidal volume; and FRC=functional residual capacity.

The open-circuit liquid ventilation systems 10, 28 according to the present invention are simplified systems, compared to known closed-circuit systems, that provide for a rapid transition between a gas-filled lung to a liquid-filled lung for a short term recruitment and conditioning of an injured or immature lung. The systems 10, 28 administer a PFC liquid to a patient, preferably utilizing a TLV technique, from a pre-packaged reservoir containing a supply of conditioned (e.g., oxygenated, warmed, and/or including a suspended drug) PFC that is appropriately sized for a particular patient (e.g., a patient having a certain weight). The open-circuit system, therefore, is adapted to provide for a single-use application with a particular patient followed by disposal of the system 10, 28 or at least a part of the system (e.g., a spent reservoir 12).

The use of TLV administration of liquid via the airways using a breathing device, as opposed to PLV or vapor/aerosol/nebulizer delivery approaches, results in a more controlled administration of liquid (pressure, volume, timing, etc.), more uniform recruitment, improved lung conditioning, and more even distribution of liquid throughout the lung. Also, when the PFC liquid is used as a carrier for a drug, there is more uniform distribution of the drug and better bioavailability when delivered by a breathing device using TLV.

Preferably, the TLV procedure is initiated by instilling PFC liquid to the gas filled lung while gently manipulating the thorax to assist removal of resident gas volumes into the expiratory line. Because gas is transported solely in dissolved form by the PFC liquid, there are no audible breath sounds and inflation pressures are minimized. The liquid volumes in the lung are monitored and controlled by the CPU of the pump 22 of systems 10, 28 to maintain effective gas exchange. Potential control strategies include constant pressure or constant flow, time-cycling, with pressure (system, airway, or alveolar) and/or volume (lung volume, tidal volume) limitation.

As described above, the liquid ventilation systems 10, 28 of the present invention provides a prepackaged assembly providing for a single-use, short term, procedure in which the lung(s) of a patient are recruited by the PFC liquid until the liquid supply contained in the prepackaged reservoir 12 has been exhausted. The goal is to provide rapid lung recruitment and conditioning for the patient over a short duration (e.g., 10 minutes) followed by a return of the patient to spontaneous breathing or to a more conventional respiratory support, such as gas ventilation, as indicated by preset respiratory markers associated with the severity of the pulmonary disorder. This approach, therefore, is distinguished from that associated with closed-circuit systems adapted for prolonged ventilatory support (e.g., hours to days).

The use of liquid ventilation to provide a short term recruitment of a lung was known. See, Greenspan et al., The Lancet, Vol. 2, Issue No. 8671, page 1095. In the described procedure, gravity and manually operated clamps were utilized to intermittently instill PFC liquid from a reservoir and to empty PFC liquid from the lungs between periods of mechanical gas ventilation. As reported, this procedure was performed in an uncontrolled, non-automated approach with no feedback on the actual ventilation parameters such as ventilation pressure and instilled lung volume for example.

In contrast, the open-circuit liquid ventilation systems 10, 28 according to the present invention provides for a short duration interruption of a subject from conventional mechanical gas ventilation (CMV) or other means of respiratory support (e.g., CPAP) while atelectatic regions of a lung are recruited and gas exchange is provided using a breathable liquid in a controlled approach. The subject is then returned to pre-existing respiratory strategy depending on the degree of lung injury. The respiratory strategy can be modified in response to improvements achieved with the breathing liquid conditioning protocol or the conditioning protocol can be repeated as required.

The present technique of using a liquid PFC under highly controlled conditions to recruit and condition a lung over a short duration followed by a return to spontaneous breathing or a conventional gas ventilator is thus a hybrid technique. The present technique incorporates some of the demonstrated and proven principles of tidal liquid ventilation (TLV). The system requirements for the present technique, however, have been modified and simplified compared to prior TLV techniques by utilizing the sealed PFC reservoir 12 containing a single-use supply of a pre-conditioned (e.g., oxygenated (potentially hyperoxygenated), warmed, free of CO2) PFC liquid that is not recycled. As a result, prime volumes are minimized and the need for specialized filtration and gas regeneration devices is eliminated.

It should be understood that the above-described short term duration of liquid ventilation provided by the open-circuit systems 10, 28 could be extended or repeated if desired. Such a repeat of the procedure might be desired, for example, if the respiratory condition of the patient to rapidly deteriorate after being returned to a gas ventilator. Extension of the initial short term recruitment period could be accomplished by replacing the spent reservoir 12 with a new sealed reservoir 12 or even by replacing the system 10, 28 having a spent reservoir 12 with another system 10, 28 having a fresh reservoir. The simplified construction of the present systems 10, 28 facilitates such replacement. Alternatively, the LAV procedure could be extended by supplementing the PFC liquid supply of the reservoir 12 with PFC liquid from another source.

It should be understood that, although PFC liquids are preferred, the present invention is not limited to any particular breathable liquid. Also, the invention is not limited to any particular type of LAV procedure. In this regard, the liquid ventilation system of the present invention could be used for drug delivery to the pulmonary system, bronchoalveolar lavage, and thermal control of a patient, for example.

As described above, the open-circuit liquid ventilation systems 10, 28 of the present invention provide servo-control over the delivery of the PFC liquid based on pressure and volume parameters monitored by the electronic sensors. The parameters monitored by the sensors preferably include tidal volume, delivery pressure, and total PFC lung volume delivered. Respiratory timing is preferably also monitored by the systems, 10, 28. The system displays feedback information to the user via the display 34 to indicate various parameters associated with proper administration of the PFC liquid (e.g., PFC volume delivered, ventilation pattern, lung mechanics and ventilation pressure profiles).

It is described above that the initial short term period (e.g., 10 minutes) provided by the one-time usage of the PFC liquid contained in the sealed reservoir 12 of systems 10, 28 could be extended, for example by replacing a spent reservoir 12 with a fresh reservoir 12, if required by the patient's condition.

Preferably, the systems 10, 28 include in-line vapor analyzers and system volume sensors. Based on vapor to liquid volume coefficients, respiratory rate and depth, the in-line vapor analyzer computes how much PFC is eliminated from the lung, thereby determining how much residual PFC liquid remains in the lung at any given time. It is desired to maintain a certain liquid volume (e.g., 10-15 mL/kg). The output from the in-line vapor analyzers helps to determine when, or if, a patient is required to be returned to liquid ventilation using one of the systems 10, 28 from the gas ventilator.

The foregoing describes the invention in terms of embodiments foreseen by the inventor for which an enabling description was available, notwithstanding that insubstantial modifications of the invention, not presently foreseen, may nonetheless represent equivalents thereto.

What is claimed:

1. An open-circuit liquid ventilation system for delivering a breathable liquid to the pulmonary system of a patient comprising:
    a reservoir containing a supply of a breathable liquid sufficient to provide for liquid ventilation of the patient in an open-circuit manner for a predetermined period of time without reconditioning of the breathable liquid;
    an expired-liquid tank for storing used breathable liquid from the pulmonary system of the patient;
    a patient interface adapted to direct the breathable liquid from the reservoir to the pulmonary system of the patient and to direct the used breathable liquid from the pulmonary system of the patient to the expired-liquid tank;
    a pump coupled between the reservoir and the patient interface for pumping the breathable liquid from the reservoir to the patient interface; and
    a controller for controlling the operation of the pump.

2. The open-circuit liquid ventilation system of claim 1, wherein the reservoir includes a container and wherein the breathable liquid is preconditioned and sealed within an interior of the container.

3. The open-circuit liquid ventilation system of claim 1, wherein the breathable liquid is a perfluorochemical.

4. The open-circuit liquid ventilation system of claim 1 further comprising an active expiration system including a bypass line connected to the pump and adapted to receive used breathable liquid from the pulmonary system of the patient such that the pump draws the used breathable liquid from the patient.

5. The open-circuit liquid ventilation system of claim 1, wherein the patient interface is adapted to provide an interface between the pulmonary system of the patient and a gas ventilation system to facilitate rapid conversion between gas ventilation of the patient and total liquid ventilation of the patient.

6. The open-circuit liquid ventilation system of claim 1, wherein the controller includes a central processing unit providing microprocessor control over the operation of the liquid ventilation system.

7. The open-circuit liquid ventilation system of claim 1 further comprising electronic sensors adapted for monitoring pressure and volume parameters associated with a liquid ventilation procedure.

8. The open-circuit liquid ventilation system of claim 1 further comprising an output display for displaying information regarding a liquid ventilation procedure.

9. The open-circuit liquid ventilation, system of claim 8, wherein the output display includes a schematic representation of the liquid ventilation system.

10. The open-circuit liquid ventilation system of claim 8. Wherein the output display includes at least one tracing representing real-time value of a pressure or volume parameter associated with the liquid ventilation procedure.

11. A method for rapidly recruiting and conditioning the pulmonary system of a patient with a breathable liquid, the method comprising the steps of:
    providing in a reservoir a volume of the breathable liquid necessary to provide for liquid ventilation of the patient for a predetermined period of time in an opencircuit manner without reconditioning of the breathable liquid;
    pumping the breathable liquid from the reservoir;
    directing the breathable liquid pumped from the reservoir into the pulmonary system of the patient via a patient interface, the breathable liquid becoming used breathable liquid after exposure to the pulmonary system of the patient; and
    directing the used breathable liquid returned from the pulmonary system of the patient to an expired-liquid tank via the patient interface.

12. The method of claim 11 further comprising the steps of:
    pumping the used breathable liquid from the pulmonary system of the patient to the expired liquid tank via the patient interface.

13. The method of claim 11 further comprising the steps of:
    providing an interface between the pulmonary system of the patient and a gas ventilation system via the patient interface; and
    converting between gas ventilation of the patient and total liquid ventilation of the patient by switching the patient interface.

14. The method of claim 11 further comprising the steps of:
    providing electronic sensors adapted to monitor pressure and volume parameters associated with a liquid ventilation procedure; and monitoring the pressure and volume parameters during a liquid ventilation procedure.

15. The method of claim 11 further comprising the steps of:
    providing an output display adapted to display information regarding a liquid ventilation procedure; and
    displaying info nation on the output display during a liquid ventilation procedure.

16. The method of claim 11 further comprising the step of:
    passively allowing the recoil pressure of the patient's pulmonary system to cause the used breathable liquid to be returned to the expired-liquid tank via the patient interface.

* * * * *